United States Patent
Cirac Sole et al.

(10) Patent No.: US 7,303,546 B2
(45) Date of Patent: Dec. 4, 2007

(54) SAFETY INSERT FOR SINGLE-USE DISPOSABLE SYRINGES

(75) Inventors: Xavier Cirac Sole, Barcelona (ES); Luis Batlló Rosés, Barcelona (ES); Ana Maria Herranz, Palleja (ES)

(73) Assignee: Tyco Electronics AMP Espana, S.A., Barcelona (ES)

(*) Notice: Subject to any disclaimer, the term of this patent is extended or adjusted under 35 U.S.C. 154(b) by 0 days.

(21) Appl. No.: 10/549,472

(22) PCT Filed: Mar. 12, 2004

(86) PCT No.: PCT/IB2004/000699

§ 371 (c)(1),
(2), (4) Date: Jul. 24, 2006

(87) PCT Pub. No.: WO2004/080514

PCT Pub. Date: Sep. 23, 2004

(65) Prior Publication Data

US 2006/0258983 A1    Nov. 16, 2006

(30) Foreign Application Priority Data

Mar. 14, 2003  (ES) ............................ 200300652 U

(51) Int. Cl.
*A61M 5/00* (2006.01)

(52) U.S. Cl. ...................................................... 604/110
(58) Field of Classification Search ................ 604/110, 604/218, 220, 236, 238, 210, 181, 187, 219, 604/221, 222, 239–243, 224
See application file for complete search history.

(56) References Cited

U.S. PATENT DOCUMENTS

| | | |
|---|---|---|
| 5,019,046 A | 5/1991 | Kohler |
| 5,021,047 A | 6/1991 | Movern |
| 5,205,825 A | 4/1993 | Allison et al. |
| 6,790,197 B2 | 9/2004 | Kosinski et al. |

FOREIGN PATENT DOCUMENTS

| | | |
|---|---|---|
| GB | 2 187 961 A | 9/1987 |
| WO | WO 83/00438 A | 2/1983 |
| WO | WO 99/44661 A | 9/1999 |

*Primary Examiner*—Manuel Mendez
(74) *Attorney, Agent, or Firm*—Barley Snyder LLC

(57) ABSTRACT

Safety insert for disposable syringes, comprising at least one attachment member whose point allows advance of the stem during injection of the syringe content and prevents its retraction once said injection is performed on attaching to the inner walls of the cylinder, and having at least one perforating member with a gaff at its end able to dig into the plunger and pass through its wall, thus breaking the tightness of the compartment of the cylinder intended to contain the substance to be injected when retraction of the stem is attempted following the injection.

5 Claims, 2 Drawing Sheets

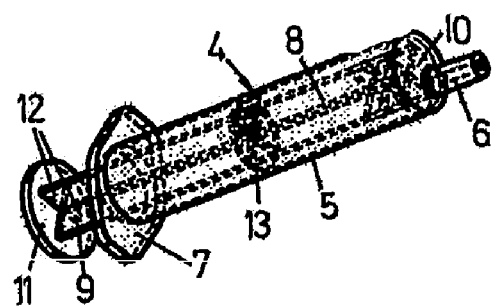
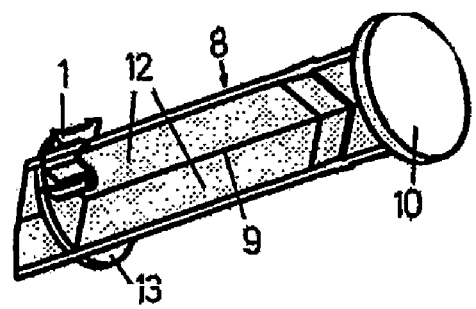
FIG. 2  FIG. 3
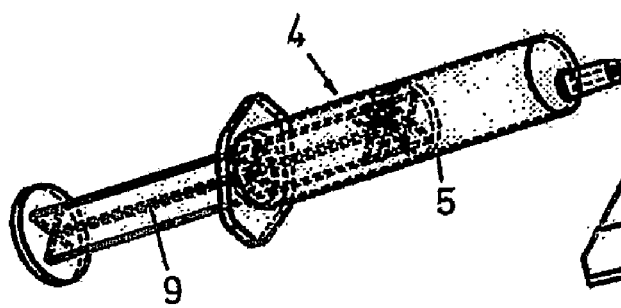
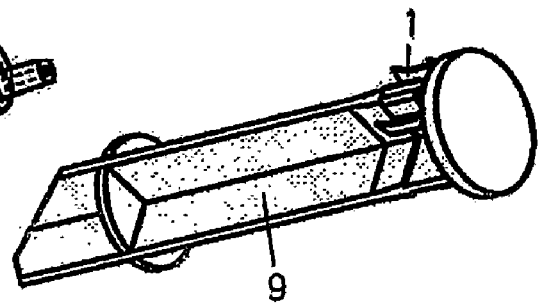
FIG. 4  FIG. 5
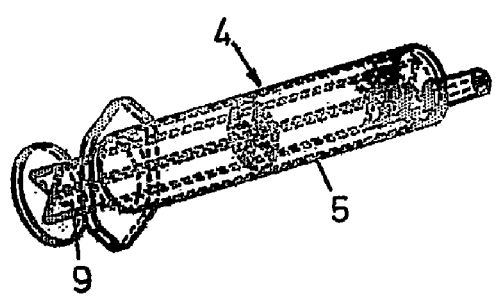
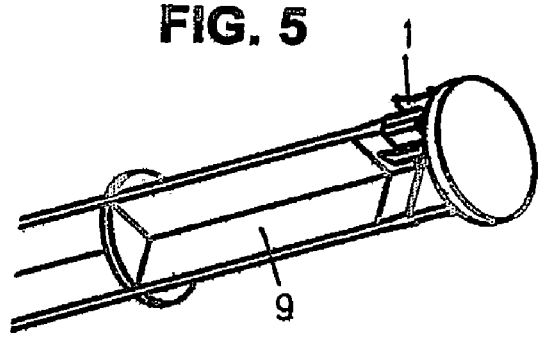
FIG. 6  FIG. 7

SAFETY INSERT FOR SINGLE-USE DISPOSABLE SYRINGES

FIELD OF THE INVENTION

The present invention relates to a safety insert for single-use disposable syringes which can be introduced into the interior thereof.

BACKGROUND

The use of disposable syringes is currently of great importance for avoiding contagion of infectious diseases, such as hepatitis or AIDS, both for health personnel and actual users of said syringes.

These syringes are very simple in construction since they usually consist of a cylindrical element and an internal element. The cylindrical element is, generally made of plastic material and has a nozzle at one end and a circular opening at the other end. The internal element has a plunger which produces a seal at one end and a base for pushing or pulling same at the other end, and a stem which joins the two aforementioned end elements.

In spite of the fact that these disposable syringes, generally made of plastic material, are sold at very low cost and are provided for single use, re-use thereof is frequent, particularly by drug addicts who inject substances intravenously, which involves an obvious and certain risk of infection.

European patent application EP 494 289 A1 describes a single-use syringe in which, by means of radial arms that are sharpened at their ends and articulated to the end of the plunger, it is possible to cut the wall of the syringe cylinder, thus breaking its seal. However, this device has the drawback that the sharp edges project externally and, while preventing reuse of the syringe, can cause infections by to potential cuts from said sharp edges.

There are numerous single-use syringes on the market which, after use, impede withdrawal of the interior plunger by mechanical means. Many of them are fixed to the syringe itself, and thus make their manufacture more expensive.

European patent EP 0 489 750 describes an insert for preventing reuse of plastic syringes. Said element can be inserted through the open end of the syringe between the internal wall of the cylindrical part of the syringe and the stem of the interior plunger. It has several tabs with points or ends which are fixed to the stem and move jointly therewith only when said stem is displaced toward the nozzle, and other tabs with points or ends, of which the inclination is such that they are fixed to the cylindrical wall when the stem is displaced away from the nozzle. A final blocked position of the nozzle is thus achieved after the syringe has been used, thus avoiding a withdrawal movement of said nozzle once the syringe has been emptied, although said construction may be sensitive to slight clearance.

SUMMARY

An object of the present invention is to provide a safety insert for disposable syringes which avoids the drawbacks of the prior art and which more reliably prevents re-use of said syringe.

It has been found that this can be achieved with means which, in the event of an attempt to withdraw the plunger after use of the syringe, break the seal of the cylindrical compartment intended to contain the substance for injection.

The invention relates to a safety insert for disposable syringes which comprises at least one perforating means with a point at its end that is capable of penetrating the plunger and passing through its wall, thus breaking the seal of the cylindrical compartment intended to contain the substance for injection when an attempt is made to withdraw the plunger after injection.

BRIEF DESCRIPTION OF THE DRAWINGS

The invention will be described below in the detailed description which makes reference to the accompanying drawings, in which:

FIG. 2 shows a perspective view of a syringe in the initial position prior to its use, FIG. 3 shows a perspective view of the insert of FIG. 1 on the interior stem and in its initial position prior to use of the syringe, without showing the cylindrical wall element, FIG. 4 shows a perspective view of a syringe after suction or filling have taken place, FIG. 5 shows a perspective view of the insert of FIG. 1 located on the interior stem in its position after suction or filling have taken place, without showing the cylindrical wall element, FIG. 6 shows a perspective view of a syringe in the final empty position, and FIG. 7 shows a perspective view of the insert of FIG. 1 located on the interior stem in its final empty position, without showing the cylindrical wall element.

DETAILED DESCRIPTION OF THE EMBODIMENTS

Figure 1:
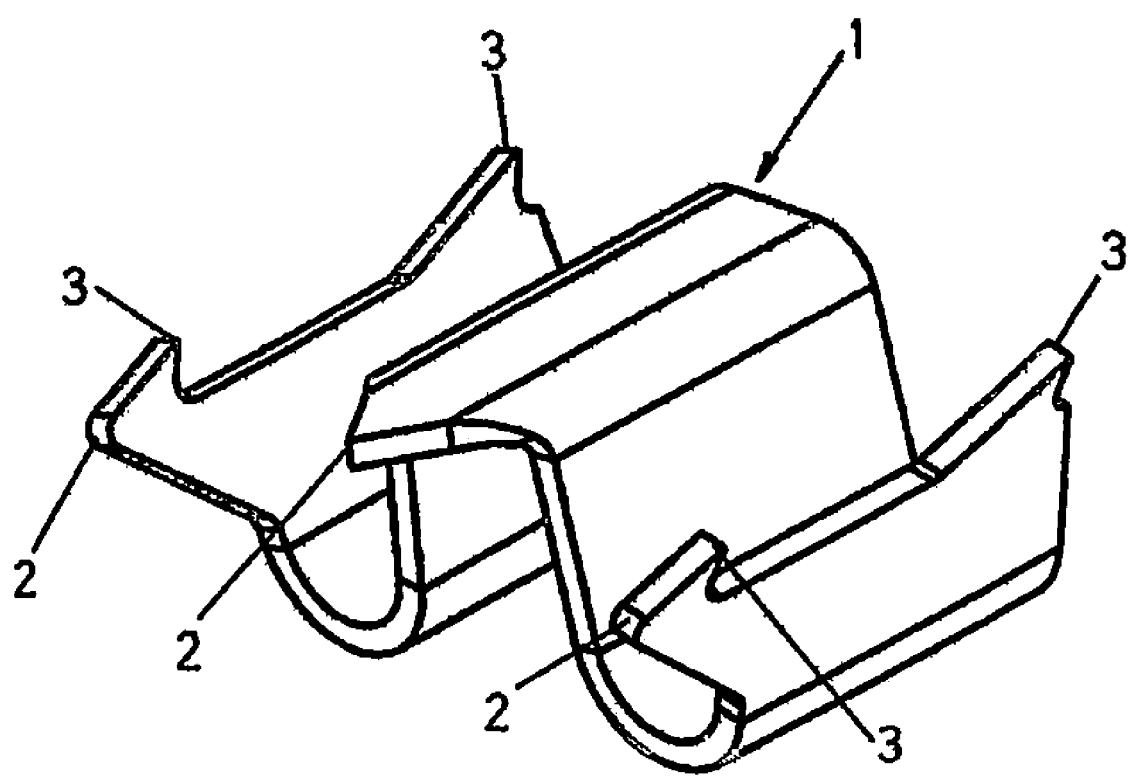
FIG. 1 shows a perspective view of an insert according to the present invention.

As can be seen in FIG. 1, the insert 1 shown in this figure has an approximately W-shaped profile and has two pairs of fixing members 3 and perforating members 2, of which two are lateral and one is central, each of them having the shape of a gaff, with their respective points. The profile of the insert 1 can have two symmetrical lateral portions and one central portion capable of settling on one of the longitudinal walls 12 of the stem 9 of the syringe 4. In said figure it can be seen that the lateral perforating are members adjacent to the respective front fixing members.

FIG. 2 shows a syringe 4 in its initial position prior to its use. Said syringe 4 has a cylindrical wall element 5 which ends at one end in a nozzle 6 and at the other end in a circular opening surrounded by a lower ring 7. The internal element 8 has, at one end, a plunger 10 and at the other end a pushing base 11, both joined by an intermediate stem 9 formed by longitudinal walls 12 with an X-shaped portion. Said stem 9 also contains at least one interior ring 13.

FIG. 3 shows the initial position of the insert 1 of FIG. 1 on said stem 9 and without showing the cylindrical wall element 5.

FIG. 4 shows the syringe 4 once suction has been produced, with total withdrawal of the stem 9. On the other hand, FIG. 5 shows the position of the insert 1 of FIG. 1 on the stem 9 of the syringe 4 once suction has been produced, without showing the cylindrical wall element 5.

FIG. 6 shows the syringe 4 once it has been emptied, with total advancement of the stem 9, and FIG. 7 shows the position of the insert 1 of FIG. 1 on the stem 9 of the syringe 4 once it has been emptied, without showing the cylindrical wall element 5.

The shape of the fixing members 3 with their respective points means that during evacuation (advancement of the stem 9), the insert 1, can advance with the stem 9 but cannot move backwards, owing to the fact that its retention members 3 impede said withdrawal by penetrating in the internal wall of the cylindrical element 5 of the syringe 4.

Therefore, on arriving at the final evacuation position the stem 9 with the insert 1, cannot move backwards and said insert 1, will remain in its end position. If there is any attempt to pull the stem 9 back with the intention of re-using the syringe 4, the perforating member 2 will penetrate on the plunger 10, passing through its wall and thus breaking the seal of the syringe 4.

The invention claimed is:

1. An insert for a single-use disposable syringe having a cylinder and a stem, the insert comprising:
    at least one fixing member, that allows advancement of the stem during injection of contents of the syringe and impedes its withdrawal once an injection has been given, by fixing itself to a wall of the cylinder; and
    at least one perforating member with a point at its end that is capable of penetrating a plunger on the stem, thus breaking the seal with the wall intended to contain the substance for injection when there is an attempt to withdraw the stem after injection;
    wherein the insert has a profile which is approximately "W" shaped.

2. The insert of claim 1 wherein the profile has two symmetrical lateral portions and one central portion capable of settling on at least one longitudinal wall of the stem.

3. The insert of claim 1 wherein the fixing member is a gaff.

4. The insert of claim 3 comprising two fixing members formed as two pairs of gaffs.

5. The insert of claim 1, wherein the perforating member comprises a central gaff located between two lateral gaffs.

* * * * *